United States Patent [19]

Hutcheson et al.

[11] Patent Number: 4,648,408
[45] Date of Patent: Mar. 10, 1987

[54] BLOOD SAMPLING UNIT

[75] Inventors: David W. Hutcheson, Grootebroek; Engelbertus J. Van Der Molen, Middenbeemster; Pieter J. Oly, Wormer, all of Netherlands

[73] Assignee: Medscan B.V., Purmerend, Netherlands

[21] Appl. No.: 731,680

[22] Filed: May 7, 1985

[30] Foreign Application Priority Data

May 11, 1984 [NL] Netherlands ............... 8401536

[51] Int. Cl.$^4$ .................................... A61B 10/00
[52] U.S. Cl. ............................... 128/770; 128/771
[58] Field of Search ............ 128/760, 770, 632, 636, 128/637, 771

[56] References Cited

U.S. PATENT DOCUMENTS

| | | | |
|---|---|---|---|
| 3,058,584 | 10/1962 | Marshall | 128/771 X |
| 3,786,510 | 1/1974 | Hodges | 128/771 X |
| 3,902,477 | 9/1975 | Gerarde | 128/760 |
| 3,990,850 | 11/1976 | Friedman et al. | 128/636 X |
| 4,360,016 | 11/1982 | Sarrine | 128/770 X |
| 4,417,891 | 11/1983 | Cianci | 128/760 X |

Primary Examiner—Kyle L. Howell
Assistant Examiner—John C. Hanley
Attorney, Agent, or Firm—Harness, Dickey & Pierce

[57] ABSTRACT

A compact disposable blood sampling unit includes at least two, preferably three main components (1, 5, 2, 3; 1, 5, 12; 14, 15, 16), which in the storage and transport position are placed on top of each other. These main components comprise a lancet (14; 25) for making a prick for blood, means for taking up blood such as a test strip (13) or a cuvette (3) and a holder (1; 20) for a desinfectant. In the storage and transport position the lancet (4; 25) is enclosed.

12 Claims, 12 Drawing Figures

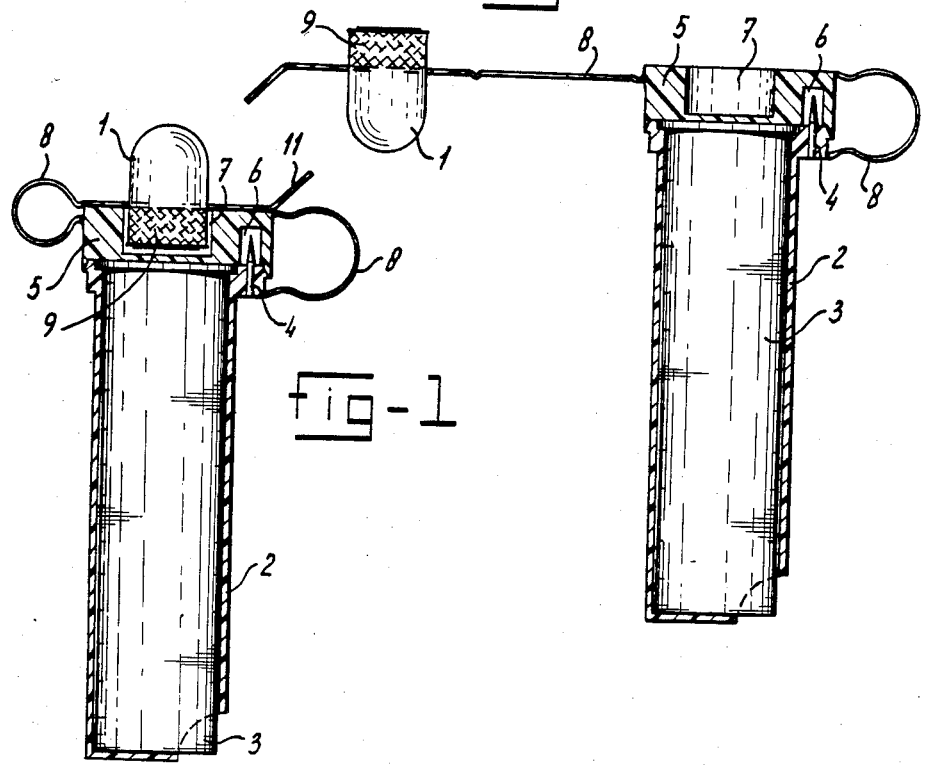
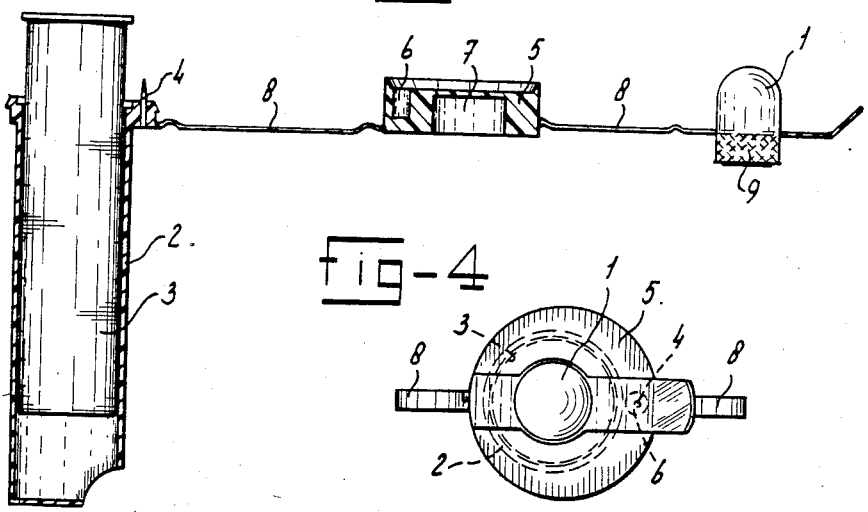
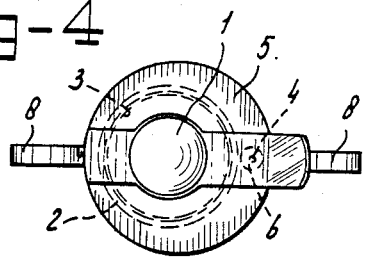

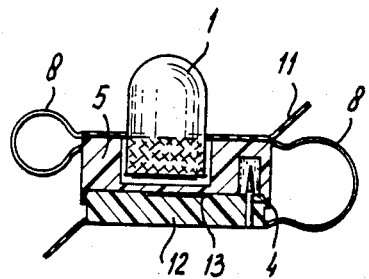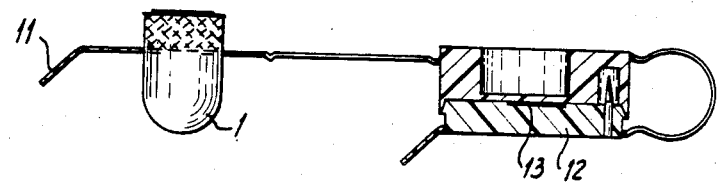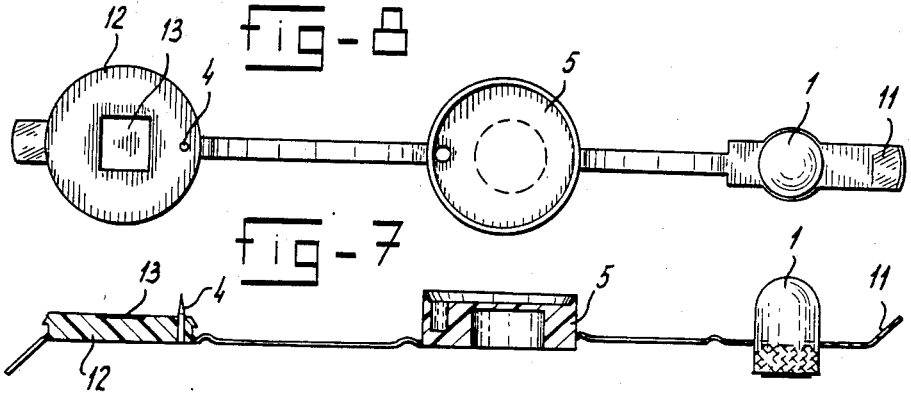

BLOOD SAMPLING UNIT

The invention relates to a blood sampling unit provided with a lancet for making a prick for blood and means for taking up blood.

Diabetics have an increased glucose level in the blood. The hormone insulin promotes the storage of glucose in the liver in the form of glycogen and converts this if necessary into fats and proteins. The most important cause of diabetes is a shortage of insulin. The treatment consists of a diet and insulin injections. It is important that diabetics are able to determine their blood sugar levels themselves and use the measured value to determine whether an insulin injection is required or not. In order to be able to determine the blood sugar level the patient must in sequence disinfect a section of the skin with a fluid suitable for this purpose, prick that section of the skin with a clean lancet, transfer one or more drops of blood to a test strip or into a cuvette, and place that strip or cuvette in a suitable analysis device. The patient must therefore always have at his disposal a small bottle of disinfecting fluid, a clean lancet, and a test strip or cuvette. Having these various items available is inconvenient and can lead to problems especially away from home.

The invention is intended to eliminate this difficulty to an important extent.

For this purpose the blood sampling unit named in the introduction is characterised in that the unit is a disposable unit which is further provided with a holder for a disinfectant and includes at least two main components which in the storage and transport position are placed on top of each other in such a manner that the lancet is enclosed.

The means or taking up blood can consist of a cuvette stored in a protective case or a small test plate which reacts with blood.

If he uses such a unit, the diabetic patient no longer has to take a separate bottle containing disinfectant and a separate box containing lancets and a separate supply of strips or cuvettes with him. These provisions are combined in a compact disposable unit, which signifies a considerable convenience for the patient. The protection of the lancet, which is mounted on a main component, may be achieved by the lancet projecting through a hole in another main component, in the enclosed state.

It is not precluded that the main components are mounted on top of each other by means of a snap-on system. It is much to be preferred, however, that hinges are used to join the main components to each other.

If the main components consist of plastic blocks, they can be manufactured cheaply in large numbers.

A very compact disposable unit which can in the main be manufactured in a single manufacturing step by injection moulding, comprises three plastic blocks joined together by narrow hinge strips, with the centre block having a blood take-up element in the form of a test strip and an opening for allowing the lancet through, which lancet is mounted on one of the other blocks in such a position that, when the blocks hinge on each other, the lancet is pushed fully through the opening until its sharp end projects in the working position.

In order that the hinge strips can be made very narrow, they are joined to the centre block at surfaces of the latter which are positioned opposite each other.

Both the small test strip and the disinfectant must be sealed from the atmosphere when the disposable unit is folded up. An easily removable means for this purpose is obtained if the block in which the holder for the disinfectant is kept and the centre block are covered by a common foil.

The user of the disposable unit will in general consider it an advantage if the unit includes a mechanism which can drive a needle through the skin of the finger at a relatively high speed. An extremely simple mechanism for this purpose is characterised by a resistance which must be overcome by the lancet or the block on which the lancet is mounted, to allow the lancet to reach the operative final position with a certain speed.

It may happen that an attempt to pierce the skin of the finger to a sufficient extent miscarries. The block which contains the lancet must then be returned to the starting position. To facilitate this block provided with the lancet may have one or more projecting parts, by means of which that block can be pushed back into the position in which the lancet or the block must overcome the resistance mentioned in order to be able to reach the operative final position. The projecting parts should also be able to fulful a function in locking the two blocks.

In a further advanced construction the lancet is joined to a leaf spring which is held in the tensioned state as a result of the fact that a part of the lancet or spring is held back behind a stop of a block, which stop belongs to a part which can be tilted by exerting force into a position in which the lancet is driven rapidly into the operative position by the leaf spring.

After the blood has acted on the small test strip (time to take effect approx. 30–60 seconds), excess blood will have to be removed. The removal of this blood by absorption can take place in an extremely simple manner if in the storage and transport position in which it is folded up, the small test strip on the centre block is covered by a means of absorption on one of the other blocks. The means of absorption consists, for example, of an absorbing tissue.

The invention will now be explained in more detail by reference to the figures, in which a number of illustrative embodiments is shown.

FIG. 1 shows a section of an initial embodiment of a blood sampling unit in which the components are in the storage position.

FIG. 2 shows a section of this embodiment in the disinfecting position.

FIG. 3 shows a section of this embodiment in the position for making a prick for blood and for taking up blood.

FIG. 4 shows a plan view of FIG. 1.

FIG. 5 shows a section of a second embodiment of a blood sampling unit in which the components are in the storage position.

FIG. 6 shows a section of a second embodiment with the components in the disinfecting position.

FIG. 7 shows a section of the second embodiment in the position for making a prick for blood and taking up blood.

FIG. 8 shows a plan view of FIG. 7.

Figure 9:
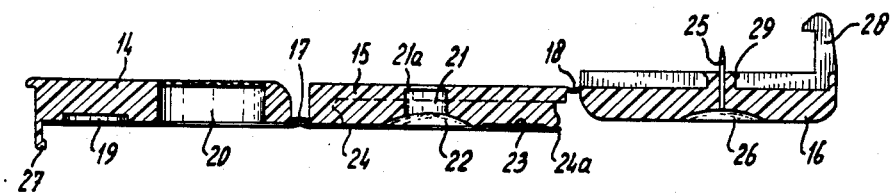
FIG. 9 shows a section of a third embodiment with the components in the opened-out state.

The blood sampling unit according to FIGS. 1 to 4 inclusive comprises a small holder 1 containing disinfecting fluid, a cuvette 3 enclosed in a protective case 2, a lancet 4 mounted in the thickened edge of the protective case 2 and a small sealing cap 5 which in the storage position according to FIG. 1 seals the inlet end of the cuvette. The small cap 5 has two recesses: a recess 7 for accommodating part of the small holder 1 and a recess 6 for accommodating the projecting part of the lancet 4.

The small holder 1, the small sealing cap 5 and the cuvette case 2 are joined together by a plastic strip 8. One of the advantages of this is that these components can be manufactured in the single working phase by injection moulding. Another advantage is that the parts 1, 2 and 5 remain together and after the unit as been used can be returned to the position according to FIG. 1, in which the lancet 4 is enclosed.

The small holder 1 is sealed by a felt stopper 9. If this small holder is manufactured from a flexible material and its walls are pressed in, it should be possible to press out the disinfecting fluid through the felt. Another possibility is that the stopper is removed and is used like a pad of cotton wool.

The plastic strip 8 forms hinges in the assembled state of the unit. The strip 8 ends in an operating lip 11.

The unit is used as follows: first the small holder 1 is hinged from the position according to FIG. 1 into the position according to FIG. 2 and a part of the skin is smeared with disinfecting fluid. The strip 8 is then fully opened out and the situation according to FIG. 3 arises. The exposed needle 4 is used to prick the sterile part of the skin and blood is deposited in the cuvette 3. The cuvette 3 is then removed from the case 2 and transferred to an analysis device. Because the cuvette 3 has been protected in the case 2 there will be no finger prints left behind on the cuvette 3 which might have effected the measurement.

The unit according to FIGS. 5–8 differs from the unit described in that the cuvette 3 with protective case 2 is replaced by a disc 12 with a small test strip 13 mounted on it which can react with a drop of blood and can then be placed in an analysis device. Usually, the analysis device is a glucometer which determines the blood sugar level, but other analyses are also possible.

Figure 10:
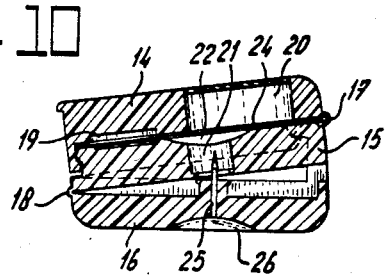
FIG. 10 shows a section of this third embodiment in the folded-up state.

The embodiment according to FIGS. 9 and 10 comprises three plastic blocks 14, 15 and 16 which are joined together by narrow hinge strips 17, 18 made of plastic material. The strips 17, 18 are joined to the centre block 15 at surfaces of the latter which are positioned opposite each other, and despite the narrow width of the hinge strips, the blocks can be folded up on top of each other as shown in FIG. 10.

Block 14 is provided with recesses 19, 20 respectively intended for an absorbing element such as a tissue and for disinfectant.

In block 15 a hole 21 has been cut out which opens into a depression 22 designed to accept the top of a finger. Moreover a small test plate 23 which reacts with blood is fixed to the surface of block 15. The blocks 14 and 15 are sealed with an aluminium foil 24 which is provided with a tab 24a at one extremity.

A lancet 25 is mounted on the block 16, for example, by molding this lancet in during a single-step injection moulding of the unit 14, 15, 16.

The position of the lancet 25 is such that when the blocks 15 and 16 are folded together it is pushed through the hole 21. In the final position the point of the needle projects past the bottom of the depression 22 but just fails to reach the level of the surface of the block 15.

The block 16 is also provided with a depression 26 in which the top of a finger or the thumb can be placed.

Diagrammatically shown are locking elements 27, 28, by means of which the blocks 14, 16 are secured with respect to the block 15 in the state in which the unit is folded together. The locking elements 28 consist of two hooks placed on the side edges of the block 16 which can engage behind laterally projecting parts of the block 15.

The lancet 25 is mounted in a raised part 29 which can act together with a circumferential ring 21a which projects inwards in the hole 21 in such a way that the raised part encounters a resistance when the blocks 15 and 16 are pressed together and the lancet, after overcoming this resistance, is driven rapidly to its final position, at which a finger top placed on the depression 22 is pricked. The projecting parts 28 have, in addition to their locking function, still another function. If making the prick for blood miscarries, the block 16 must be returned to the starting position in which the resistance has to be overcome in order to allow the lancet to be able to reach the operative final position. This returning of block 16 to the starting position can be achieved through the parts 28 being pressed back by means of the block 14 until the position according to FIG. 10 is reached.

It will be clear that the unit according to FIGS. 9 and 10 is used as follows: after the unit has been folded open and the foil 24 removed, a finger top is disinfected by means of the disinfectant contained in the holder 20. This finger top is then placed on the depression 22, after which the block 16 is folded onto the block 15 by means of a finger or thumb placed on the depression 26, as a result of which the lancet pricks the disinfected finger top. A drop of blood is transferred to the small test disc 23 which undergoes a discolouration in the course of approximately one minute as a result. Excess blood is removed by folding the block 14 against the block 15, as a result of which the absorption element, which, for example, consists of a tissue, in the recess 19 is brought into contact with the small test plate 23 and absorbs the blood. The degree of discolouration is a measure of the blood surgar level and this can be determined by means of a so-called glucometer or coloured strip. After use the unit is thrown away.

Figure 11:
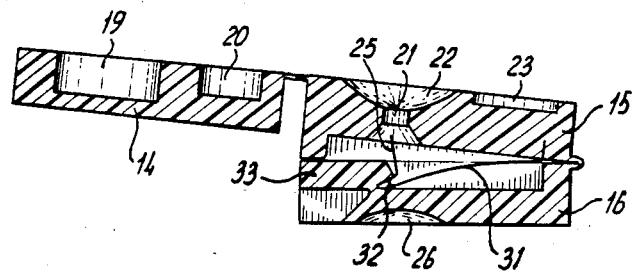
FIG. 11 shows a section of a fourth embodiment with a spring-tensioned drive mechanism for the lancet, the lancet being in the triggered position.
Figure 12:
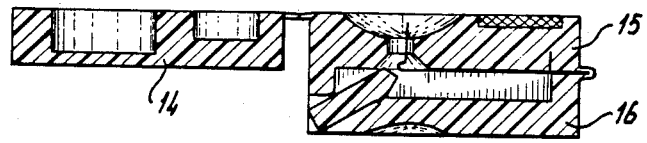
FIG. 12 shows a section of the fourth embodiment in which the lancet is in the prick position.

The embodiment according to FIGS. 11 and 12 differs from those according to FIGS. 9 and 10 through the presence of a spring-loaded trigger mechanism for the lancet 25. For this purpose the lancet is joined to a leaf spring 31 which is provided with a projection 32 which in the triggered position is secured behind a tiltable part 33 of the block 16. As FIG. 12 shows, by pressing the block 16 against the block 15 the part 33 will tilt, as a result of which the projection 32 of the leaf spring is no longer held back and the lancet is driven by the leaf spring at high speed to the position at which a finger top placed on the depression 22 is pricked.

Within the scope of the invention various modifications are possible. An essential feature of the invention is that the provisions which are necessary for the taking of blood samples are combined in a compact disposable unit, which unit consists of at least two, preferably three, parts or blocks, which in the storage and transport position are placed on top of each other in a manner such that the lancet is enclosed. The unit is not limited to determining the glucose level in the blood.

Other blood samplings are also possible, for example for determining the cholesterol level, pregnancy and the like.

We claim:

1. A disposable blood sampling unit comprising three blocks connected to each other by hinged portions for movement between an open, operative position and a closed, storage position, one of said blocks carrying a lancet for pricking the skin of a user for draining a blood sample, another of said blocks defining a cavity for receiving said lancet when said blocks are in their closed storage position to protect said lancet, one of said blocks defining a recess for receipt of a disinfectant, and one of said blocks having means for accepting a blood sample from a user.

2. A blood sampling unit as set forth in claim 1 wherein the means for accepting a blood sample comprises a tube adapted to receive the user's blood.

3. A blood sampling unit as set forth in claim 2 wherein the tube is removable from the one block.

4. A blood sampling unit as set forth in claim 1 wherein the means for accepting a blood sample comprises a test strip carried by the one block.

5. A blood sampling unit as set forth in claim 4 further including a piece of foil affixed to the one block and overlying the test strip, said piece of foil being provided with tab means for its ready removal.

6. A blood sampling unit as set forth in claim 5 wherein the foil strip overlies the recess receiving the disinfectant.

7. A blood sampling unit as set forth in claim 6 wherein the block carrying the test strip and the block carrying the disinfectant are different blocks.

8. A blood sampling unit as set forth in claim 1 wherein the cavity in the other of the blocks opens through one of its faces and further terminates at a finger receiving portion at the other of its faces.

9. A blood sampling unit as set forth in claim 8 wherein the lancet does not normally extend into the finger receiving portion of the other block when the one block and the other block are in a first position and further including yieldable biasing means for releasably restraining the one block and the other block in the first position and for permitting a user to press the block to another position wherein the lancet enters the finger receiving recess for piercing the skin of the user.

10. A blood sampling unit as set forth in claim 9 wherein the releasably restraining means comprises a portion on the one block adapted to enter into the first portion of the cavity on the other block.

11. A blood sampling unit as set forth in claim 9 wherein the releasable restraining means comprises a releasable latching means.

12. A blood sampling unit as set forth in claim 9 wherein the lancet is normally biased to a retracted position and is spring urged to enter into the finger receiving portion for piercing the skin of a user.

* * * * *